US008716532B2

(12) United States Patent
Sharma et al.

(10) Patent No.: US 8,716,532 B2
(45) Date of Patent: May 6, 2014

(54) ONE POT MULTICOMPONENT SYNTHESIS OF SOME NOVEL HYDROXY STILBENE DERIVATIVES WITH ALPHA, BETA-CARBONYL CONJUGATION UNDER MICROWAVE IRRADIATION

(75) Inventors: Abhishek Sharma, Palampur (IN); Arun Kumar Sinha, Palampur (IN); Rakesh Kumar, Palampur (IN); Naina Sharma, Palampur (IN)

(73) Assignee: Council of Scientific and Industrial Research, New Delhi (IN)

( * ) Notice: Subject to any disclaimer, the term of this patent is extended or adjusted under 35 U.S.C. 154(b) by 202 days.

(21) Appl. No.: 13/260,806

(22) PCT Filed: Mar. 26, 2010

(86) PCT No.: PCT/IB2010/000675
§ 371 (c)(1),
(2), (4) Date: Mar. 5, 2012

(87) PCT Pub. No.: WO2010/113005
PCT Pub. Date: Oct. 7, 2010

(65) Prior Publication Data
US 2012/0165567 A1    Jun. 28, 2012

(30) Foreign Application Priority Data
Mar. 31, 2009    (IN) .............................. 661/DEL/2009

(51) Int. Cl.
*C07C 39/215* (2006.01)

(52) U.S. Cl.
USPC ............ 568/729; 568/650; 568/659; 568/660

(58) Field of Classification Search
USPC ................................. 568/729, 650, 659, 660
See application file for complete search history.

(56) References Cited

U.S. PATENT DOCUMENTS

| | | | |
|---|---|---|---|
| 4,371,475 A | 2/1983 | Yanagisawa et al. | |
| PP4,996 P | 3/1983 | Meserve | |
| 5,210,165 A * | 5/1993 | Hall et al. ................... | 526/300 |
| 5,569,786 A | 10/1996 | Pettit et al. | |
| 6,048,903 A | 4/2000 | Toppo | |
| 6,361,815 B1 | 3/2002 | Zheng | |
| 6,521,669 B1 | 2/2003 | Liviero et al. | |
| 6,552,213 B1 | 4/2003 | Deshpande et al. | |
| 6,844,471 B2 | 1/2005 | Deshpande et al. | |
| 6,989,467 B2 | 1/2006 | Sinha | |
| 2002/0197274 A1 | 12/2002 | Shiao et al. | |
| 2003/0073712 A1 | 4/2003 | Wang et al. | |
| 2003/0086987 A1 | 5/2003 | Shiao et al. | |
| 2004/0015020 A1 | 1/2004 | Deshpande | |
| 2004/0147788 A1 | 7/2004 | Savouret et al. | |
| 2004/0152629 A1 | 8/2004 | Hadfield et al. | |
| 2005/0234261 A1 * | 10/2005 | Wilken et al. ................. | 560/129 |
| 2007/0276172 A1 | 11/2007 | Sinha | |

FOREIGN PATENT DOCUMENTS

| | | |
|---|---|---|
| CH | 500145 A | 12/1970 |
| EP | 0433449 A1 | 6/1991 |
| EP | 0331983 B1 | 12/1994 |
| EP | 1068864 A1 | 1/2001 |
| GB | 1222863 A | 2/1971 |
| WO | 2004000302 A1 | 12/2003 |
| WO | 2007/110883 A1 | 10/2007 |

OTHER PUBLICATIONS

Wang et al; Colloids and Surfaces A: Physicochemical Engineering Aspects 276 (2006) 116-121.*
Kumar et al; Tetrahedron 63 (2007) 7640-7646.*
Saravanan S et al: "Microwave-Induced Synthesis of Nitrostilbenes Under Neat Condition" Synthetic Communications, Taylor & Francis Group, Philadelphia, PA LNKD-DOI: 10.1081/SCC-100103315, vol. 31, No. 6, Mar. 1, 2001, pp. 823-826.
Hoag B P et al: "Polymerizable Hexacatenar Liquid Crystals Containing a Luminescent Oligo (P-Phenylenevinylene) Core"—Liquid Crystals: An International Journal of Science and Technology. Taylor & Francis, GB, vol. 31. No. 2. Feb. 1, 2004, pp. 185-199.
Mates T E et al: :"New Thermotropic Polyesters From Distyrylbenzene Bisphenols" Journal of Polymer Science, Polymer Letters Edition, John Wiley and Sons, New York, US, vol. 28. Jan. 1, 1990, pp. 331-339.
Emilia Evangelio et al.: "Catechol Derivatives as Fluorescent Chemosensors for Wide-Range pH Detection" Chemistry—A European Journal, vol. 14, No. 31, Nov. 11, 2008, pp. 9754-9763.
Jung et al: "Design, synthesis, and discovery of stilbene derivatives based on lithospermic acid B as potent protein tyrosine phosphatase 1B inhibitors". Bioorganic & Medicinal Chemistry Letters, Pergamon, Elsevier Science, vol. 17, No. 16, Jul. 17, 2007, pp. 4481-4486.
Kumar et al: "Remarkable synergism in methylimidazole-promoted decarboxylation of substituted cinnamic acid derivatives in basic water medium under microwave irradiation: a clean synthesis of hydroxylated (E)-stilbenes". Tetrahedron. Elsevier Science Publishers, Amsterdam, vol. 63, No. 32, Jun. 22, 2007, pp. 7640-7646.
Schultz T P et al: "Structure-fungicidal properties of some 3- and 4-hydroxylated stilbenes and bibenzyl analogues". Phytochemistry, Pergamon Press, vol. 31, No. 11, Jan. 1, 1992, pp. 3801-3806.
International Search Report mailed Mar. 25, 2011 (PCT/IB2010/000675): ISA/EP.
International Preliminary Report on Patentability mailed Aug. 22, 2011 (PCT/IB2010/000675); IPEA/EP.

* cited by examiner

*Primary Examiner* — Johann R Richter
*Assistant Examiner* — Pancham Bakshi
(74) *Attorney, Agent, or Firm* — Banner & Witcoff, Ltd.

(57) ABSTRACT

The present invention provides a method for the preparation of some novel multiconjugated 2- or 4-hydroxy substituted stilbenes. The method provides one pot multicomponent approach wherein 3-4 step reaction sequences viz. condensation, decarboxylation and Heck coupling occur simultaneously which results in an enhanced yield of desired products and reduced reaction times.

13 Claims, 2 Drawing Sheets

4-((*E*)-prop-2-enoic acid)-3', 4'-dihydroxystilbene
Fig.1

4-((*E*)-prop-2-enoic acid)-4'-hydroxy-3', 5'-dimethoxystilbene
Fig.2

2'-(propyl)-4-hydroxy-3, 4', 5'-trimethoxystilbene
Fig.3

4-hydroxy-3,4',5-trimethoxy stilbene
Fig.4

4-hydroxy-3-methoxy, 3',4'-dioxymethylene stilbene
Fig.5

2-(4-hydroxy-3-methoxystyryl)thiophene
Fig.6

1-(4-methoxyphenyl)-2-(2-naphthyl) ethane
Fig.7

(*E,E*)-1,4-Bis(4-hydroxy, 3-methoxy)styrylbenzene
Fig.8

(*E,E*)-1,4-Bis(4-hydroxy, 3,5-dimethoxy)styrylbenzene
Fig.9

(E,E,E)-1,3,5-Tris(4-hydroxy, 3,5-dimethoxy)styrylbenzene

Fig.10

(E,E)-9,10-Bis(4-hydroxy, 3,5-dimethoxy)styrylanthracene

Fig.13

(E,E)-4,4'-Bis(4-hydroxy-3,5-dimethoxy)styrylbiphenyl

Fig.11

(E,E)-2-Fluoro-1,4-bis(4-hydroxy-3,5 dimethoxy)styrylbenzene

Fig.14

(E,E)-1,4-Dimethoxy-2,5-bis(4-hydroxy-3-methoxy)styrylbenzene

Fig.12

4-hydroxy-3-methoxy-4'-(3-(1-(4-methoxyphenyl))-2-propen-1-one)stilbene

ONE POT MULTICOMPONENT SYNTHESIS OF SOME NOVEL HYDROXY STILBENE DERIVATIVES WITH ALPHA, BETA-CARBONYL CONJUGATION UNDER MICROWAVE IRRADIATION

CROSS-REFERENCE TO RELATED APPLICATIONS

The present application is a U.S. National Phase filing of International Application No. PCT/IB2010/000675 filed on Mar. 26, 2010, designating the United States of America and claiming priority to India Patent Application No. 661/DEL/2009, filed Mar. 31, 2009, both of which applications the present application claims priority to and the benefit of, and both of which are incorporated by reference herein in their entireties.

The following specification particularly describes the nature of this invention and the manner in which it is to be performed:

FIELD OF INVENTION

The present invention provides a process for one pot multi component synthesis of some novel hydroxy stilbene derivatives with α, β-carbonyl conjugation under microwave irradiation. The invention particularly relates to the preparation of some novel commercially important multiconjugated 2 or 4-hydroxy substituted stilbenes including lithospermic acid based stilbene analogues possessing an α, β-unsaturated carboxylic acid moiety i.e. ($C_6$—$C_2$—$C_6$—$C_3$ chain) and wide ranging applications as potent pharmacophores for diverse ailments including diabetes and cardiovascular disorders besides finding usage in non-linear optical devices and optoelectronics.

BACKGROUND

Stilbene and its derivatives have been widely reported to possess a plethora of industrial and pharmaceutical applications. In particular, the hydroxy substituted stilbenoids have been found to be privileged structural motifs in diverse bioactive natural products. For instance, various dihydroxy stilbene derivatives based on lithospermic acid, a polyphenolic compound found in *Salvia miltorrhiza* (*Planta Med.* 1984; 50, 227-228, *Phytochemistry* 1994, 37, 907-908) have been implicated as potent antidiabetic agents as they display significant inhibitory activity against protein tyrosine phosphatase (PTP1B) enzyme (*Bioorg. Med. Chem. Lett.* 2007, 17, 4481). Similarly, the salvionolic acid derivatives, isolated from genus *Salvia*, have been widely studied and ascribed numerous biological activities including antitumoral, antiinflammatory, gastric and antioxidant activities (US 2003/0086987A1 and US 2002/0197274A1). In yet another instance, the multiconjugated stilbenes like 1,4-bis-styryl-benzenes are reported to possess important applications as in vivo magnetic resonance imaging agents for diagnosis and monitoring of various neurodegenerative ailments like Alzheimer's disease owing to their strong amyloid fibril (Aβ) plaque binding ability (*J. of Med. Chem.,* 2007, 50, 4986). In addition, the 1,4-bis-styrylbenzenes have also been used as optical brighteners (U.S. Pat. No. 4,371,475). Similarly, resveratrol, a phytoalexin, present in grapes and other fruits (J. Burns, T. Yokota, H. Ashihara, M. E. J. Lean, A. Crozier, *J. Agric. Food Chem.,* 2002, 50, 3337; G. J. Soleas, E. P. Diamandis, D. M. Goldberg, *Clin. Biochem.,* 1997, 30, 91); resveratrol (3,4',5-trihydroxy-(E)-stilbene) and a major component of red wine, has been implicated as a potent cardioprotective agent, thus lending credence to the conjecture that red wine consumption retards cardio-vascular mortality. In addition, several epidemiological and immunological studies have identified resveratrol as a potent therapeutical agent for Alzheimer's disease and cancer (*Science,* 1997, 275, 218). Combretastatin A-4, a stilbene isolated from the African bush willow, *Combretum*, has been found to be a potent anti-cancer agent, binding strongly to tubulin and displaying selective toxicity towards tumor vasculature (U.S. Pat. No. 4996; *Brit. J. Cancer,* 1999, 81, 1318; *Brit. J. Cancer,* 1995, 71, 705). Combretastatin A-4 is able to elicit irreversible vascular shutdown within solid tumors, leaving normal vasculature intact (E. Hamel, C. M. Lin, *Biochem. Pharmacol.,* 1983, 32, 3863; D. J. Chaplin, G. R. Pettit, C. S. Parkins, S. A. Hill, Brit. *J. Cancer,* 1996, 74, S86; G. G. Dark, S. A. Hill, V. E. Prise, G. M. Tozer, G. R. Pettit, D. J. Chaplin, *Cancer Res.,* 1997, 57, 1829). In addition, intensive investigations of several other stilbenes have brought forth their immense potential as versatile pharmacophores (Pettit, G. R.; Grealish, M. P.; Jung, M. K.; Hamel, E.; Pettit, R. K.; Chapuis, J. C.; Schmidt, J. M. *J. Med. Chem.,* 2002, 45, 2534-2542; Kim, S.; Ko, H.; Park, J. E.; Jung, S.; Lee, S. K.; Chun, Y.-J. *J. Med. Chem.,* 2002, 45, 160-164). In view of their immense medicinal importance, there have been numerous efforts at devising efficient synthetic methodologies towards 2- or 4-hydroxy substituted stilbene derivatives and their analogues. For instance, 3,4 dihydroxy styryl cinnamate, a lithospemic acid based antidiabetic stilbene derivative, has been synthesized through a lengthy 9 step synthetic strategy via Wittig olefination of corresponding hydroxy benzaldehydes. The presence of the hydroxy function in target compounds not only required additional protection-deprotection steps but also precluded the use of any alternate synthetic strategy (*Bioorg. Med. Chem. Lett.* 2007, 17, 4481). Similarly, the naturally occurring salvianolic acid was synthesized in a tedious 8 step linear reaction sequence involving protection of hydroxy function, Wittig olefinations and deprotection of the hydroxy group which results in a significant decrease in the overall synthetic efficiency (*Tetrahedron* 55 (1999) 6923-6930). In yet another instance, a majority of the conventional synthetic methods for medicinally important 1,4-bis-styrylbenzenes comprise tedious multistep sequences involving wittig, and protection, deprotection strategies (*J. Med. Chem.* 2007, 50, 4986-4992).

Various other commercially important stilbene derivatives have been accessed through diverse reaction methodologies, including Wittig, modified Julia olefination, reaction of benzyllithium with benzaldehydes followed by dehydration, Perkins reaction, cross metathesis of styrenes, Suzuki reaction with β-halostyrenes, decarbonylative Heck reaction between acid chloride and styrene, Heck arylation-desilylation of vinylsilane followed by Heck arylation of styrenes formed in situ and palladium catalysed arylation of styrenes with halobenzene (G. R. Pettit, M. P. Grealish, M. K. Jung, E. Hamel, R. K. Pettit, J.-C. Chapuis, J. M. Schmidt, *J. Med. Chem.,* 2002, 45, 2534; M. Roberti, D. Pizzirani, D. Simony, R. Rondanin, R. Baruchello, C. Bonora, F. Buscemi, S. Grimaudo, M. Tolomeo, *J. Med. Chem.,* 2003, 46, 3546; H. Meier, U. Dullweber, *Tetrahedron Lett.,* 1996, 37, 1191; J. Yu, M. J. Gaunt, J. B. Spencer, *J. Org. Chem.,* 2002, 67, 4627; D. A. Alonso, C. Nájera, M. Varea, *Tetrahedron Lett.,* 2004, 45, 573; E. Alonso, D. J. Ramón, M. Yus, *J. Org. Chem.,* 1997, 62, 47; G. Solladié, Y. Pasturel-Jacopé, J. Maignun, *Tetrahedron,* 2003, 59, 3315; S. Chang, Y. Na, H. J. Shin, E. Choi, L. S. Jeong, *Tetrahedron Lett.,* 2002, 43, 7445; S. Eddarir, Z. Abdelhadi, C. Rolando, *Tetrahedron Lett.,* 2001, 42, 9127; M. B. Andrus, J. Liu, E. L. Meredith, E. Nartey, *Tetrahedron*

Lett., 2003, 44, 4819; T. Jeffery, B. Ferber, *Tetrahedron Lett.*, 2003, 44, 193; N. F. Thomas, K. C. Lee, T. Paraidathathu, J. F. F. Weber, K. Awing, *Tetrahedron Lett.*, 2002, 43, 3151).

The following prior art references are disclosed as below:

*Journal of Org. Chem.*, 2001, 66, 8135, discloses a method for the synthesis of combretastatin A-4 (both cis and trans isomeric forms) through Wittig method and Perkin condensation method.

*Natural Product Research.*, 2006, 20, 247, discloses a method for the improved synthesis of resveratrol through two step process Wittig reaction and Heck coupling. *Synthesis*, 2006, 273, discloses a method for the synthesis of biologically important trans-stilbenes via Ru-catalyzed cross metathesis.

*J. Med. Chem.*, 2005, 48, 6783, discloses a method for the synthesis of resveratrol analogue with high ceramide-mediated proapoptotic activity on human breast cancer cells.

*Molecules*, 2004, 9, 658, discloses a method for synthesis of stilbenes via the Knoevenagel condensation.

*Carbohydrate Research.*, 1997, 301, 95, discloses a method for the synthesis of hydroxy stilbenes and their glycosides through Wittig reaction.

*Bioorg. Med. Chem. Lett.* 1998, 8, 1997, discloses a method for the asymmetric synthesis of antimitotic combretadioxolone with potent anti-tumor activity.

*Tetrahedron*, 2004, 60, 5563, discloses a method for the synthesis of resveratrol and their analogues using Heck reaction in organic and aqueous solvents.

*J. Med. Chem.*, 2002, 45, 2534, discloses a method for the synthesis of hydroxy stilbenes and benzophenones through Wittig reaction.

U.S. Pat. No. 20040147788 A1 discloses a method for the synthesis of stilbene derivatives through Wittig reaction.

U.S. Pat. No. 20040015020 A1 discloses a method for the synthesis of E-isomer of stilbene through halide assisted conversion of corresponding Z-isomer.

*J. Med. Chem.*, 2003, 46, 3546, discloses a method for the synthesis of resveratrol and their analogues through addition of aromatic aldehydes and appropriate ylide.

*Journal of Org. Chem.*, 1961, 26, 5243, discloses a method for the synthesis of stilbene and heterocyclic stilbene analogues.

*Journal of Chem. Soc.*, 1954, 3596, discloses a method for the synthesis of stilbenes through dehydrogenation from diarylethanes.

U.S. Pat. No. 6,048,903 discloses a method for the synthesis of E-resveratrol by Wittig reaction comprising benzyltriaryl phosphonium salt and anisaldehyde in the presence of n-butyl lithium.

*Organic Synthesis Collective Volume* I, 1941, 441-442 and Volume IV, 1963, 731-734, disclose a method for the preparation of styrenes by decarboxylation of cinnamic acids with quinoline in the presence of copper powder at 200-300° C.

Some of other typical prior art references include U.S. Pat. Nos. 6,844,471, 6,552,213, 20040152629 A1; 6361815; 5569786; European Pat. Nos. EP 0331983; *Tetrahedron lett.*, 1980, 21, 2073; *Synthesis*, 1977, 58, *J. Chem. Soc. Perkin Trans.* I, 1974, 961; *J. Chem. Soc.*, 1963, 2875; *Chem. Pharm. Bull.*, 1992, 40, 1130; *Bioorg. Med. Chem. Lett.* 2007, 17, 4481, *Tetrahedron* 55 (1999) 6923-6930.

Amongst the above mentioned synthetic methodologies for hydroxy stilbenes, the palladium catalysed Heck reaction between hydroxy styrenes and halobenzenes has remained a prominent approach due to the easy availability of variously substituted halobenzenes, remarkable ability of palladium catalyst to withstand a wide range of functional groups coupled with the possibilty to conduct multicomponent reactions using appropriately substituted reactants. However, the Heck approach for hydroxy substituted stilbenes has also been recognized to be tedious and inefficient due to the preponderant tendency of hydroxy styrenes for polymerization. Consequently, a majority of the prevalent Heck approaches for hydroxy stilbenes comprise multistep protection-deprotection sequences (Natural Product Research, Vol. 21, No. 6, 20 May 2007, 564-573, Natural Product Research, Vol. 20, No. 3, March 2006, 247-252, Tetrahedron Letters 47 (2006) 5811-5814.) which not only utilize harsh reagents but also further burden the overall synthetic efficiency of the method.

In order to address the above concerns, it therefore, becomes an object of the invention to develop a method, wherein the hydroxy styrenes are formed from the corresponding benzaldehydes, cinnamic acids or their derivatives and then allowed to react in situ with appropriately substituted halobenzenes under Heck like conditions to give the desired stilbene derivatives without any need for isolation of reaction intermediates or protection-deprotection steps. The above one pot approach would not only remove the currently indispensable and synthetically inefficient isolation of reaction intermediates obtained from sequential condensation, decarboxylation and Heck reactions but also provide the desired stilbenes in enhanced yields as it would allow the hydroxystyrenes to in situ join the desired Heck coupling pathway instead of the competing wasteful polymerization pathways.

It is worthwhile to mention that we had earlier disclosed a microwave induced process for the preparation of substituted stilbenes and its analogs (U.S. Patent No. 20070276172 A1). However, the above approach employing Perkin reaction between hydroxy benzaldehydes and phenyl acetic acids was limited towards the synthesis of stilbenes ($C_6$—$C_2$—$C_6$ chain) possessing a single ethylinic linkage which severely precluded an access towards immensely important multiconjugated stilbenes possessing an α, β-unsaturated carboxylic acid moiety i.e. ($C_6$—$C_2$—$C_6$—$C_3$ chain). In contrast, such an introduction of extra $C_3$ chain to stilbene moiety ($C_6$—$C_2$—$C_6$ chain) is not possible using our above patent (U.S. Patent No. 20070276172 A1). Further, the present invention not only gives a new one pot approach towards Heck coupling of in situ formed hydroxy styrenes, but also provides an unprecedented opportunity to conduct simultaneous multicomponent reactions in one pot leading to a novel single step synthesis of a range of medicinally important multiconjugated stilbene derivatives including antidiabetic lithospermic acids etc. which had hitherto been accessed only through tedious multistep protocols.

In view of the above discussion, it is quite evident that there is a need for developing efficient synthetic protocols for hydroxy substituted stilbene derivatives and analogues in view of the current limitations like lengthy mutistep protocols, use of harsh protection-deprotection reagents and low yields of final products etc. It, therefore, becomes an object of the invention to provide a rapid, economical and one pot multicomponent process for the preparation of 2- or 4-hydroxy substituted stilbene derivatives from cheap and commercially available substituted arylaldehydes and halobenzenes so as to eliminate the disadvantages associated with the above patents and papers. It is worthwhile to mention that microwave-assisted (A. K. Bose, B. K. Banik, N. Lavlinskaia, M. Jayaraman, M. S. Manhas, *Chemtech*, 1997, 27, 18; M. Larhed, Hallberg, *Drug Discovery Today*, 2001, 6(8), 406) chemical transformation is a new emerging technique which is generally known for ecofriendly, rapid and high yielding process. However, such an effect of microwave is unique in the above invention in a way that a one pot multicomponent reaction involving condensation, decarboxylation and Heck coupling would occur simultaneously without either the need for decarboxylation/protection-deprotection agents or isolation of highly reactive intermediates.

Keeping in view the above problems, we disclose a unique and novel one pot process to prepare 2- or 4-hydroxystilbene derivatives and their analogues in one step from 2- or 4-hydroxy substituted arylaldehydes, malonic acid and halobenzenes in the presence of a base, palladium catalyst, triphenylphosphine and solvent. In fact, we have already observed that while trying to emulate Knoevenagel Doebner condensation (B. S. Furniss, A. J. Hannaford, V. Rogers, P. W. G. Smith, A. R. Tatchell, In: *Vogel's Textbook of Practical Organic Chemistry*, Fourth Edn. (ELBS, UK), 1978, 802), reaction under microwave (A. K. Bose, B. K. Banik, N. Lavlinskaia, M. Jayaraman, M. S. Manhas, *Chemtech,* 1997, 27, 18; M. Larhed, Hallberg, *Drug Discovery Today,* 2001, 6(8), 406; C. Kuang, H. Senboku, M. Tokuda, *Tetrahedron,* 2002, 58, 1491; N. Kuhnert, *Angew. Chem. Int. Ed,* 2002, 41, 1863), 4-hydroxy substituted benzaldehydes produce aryl styrenes instead of the expected cinnamic acids (A. K Sinha., B. P Joshi., A Sharma., U.S. Pat. No. 6,989,467, 2006). The above finding coupled with the limitation of using hydroxy styrene in a linear reaction sequence for a Heck type synthesis of stilbene derivatives prompted us to explore a one pot multicomponent strategy wherein hydroxy styrenes are initially formed and then allowed to couple in situ with appropriately substituted halobenzenes to give diverse bioactive compounds bearing the stilbene scaffold. Hence, in the beginning, we decided to react 3,4-dihydroxy benzaldehyde with malonic acid and bromobenzaldehyde in a unique one pot Knoevenagel Doebner Heck reaction methodology utilizing a base, palladium catalyst and triphenylphosphine under microwave irradiation. To our delight, our above premise was proven when the expected product, a novel multiconjugated stilbene cinnamic acid derivative was formed in a short reaction time albeit in a low yield. Thereafter, the amount of malonic acid was increased and various combinations of bases, palladium catalyst and solvents were used to optimize the reaction conditions which produced the product in moderate to good yield. The same method was applied on other 2- or 4-hydroxy substituted benzaldehydes which upon condensation with malonic acid and subsequent coupling with various substituted halobenzenes, successfully provided various other novel multiconjugated stilbene derivatives, wherein, three or more reaction steps involving condensation, decarboxylation, and Heck coupling got completed in a single step.

OBJECTIVES OF THE INVENTION

The main object of the present invention is to provide a method for the one pot multicomponent synthesis of some novel multiconjugated hydroxy stilbene derivatives under microwave irradiation.

Another object of the present invention is to prepare some immensely important bioactive hydroxy stilbene derivatives including analogues of lithospermic acid (3,4-dihydroxy styrylcinnamate), bis-styrylbenzenes, salvionilic acid etc. by conducting a series of multicomponent reactions in the same pot.

Yet another object of the present invention is to provide a process for the preparation of 2- or 4-hydroxy substituted stilbene derivatives under microwave or conventional conditions.

Yet another object of the present invention is to provide a process for the preparation of 2- or 4-hydroxy substituted stilbene derivatives wherein condensation, decarboxylation and Heck coupling occurred in one step without addition of decarboxylating agent or the need for isolation of reaction intermediates.

Yet another object of the invention is to provide a process to prepare 2- or 4-hydroxy substituted stilbene derivatives without the use of harsh protection-deprotection reagents.

Yet another object of the invention is to provide a simple process for the preparation of 2- or 4-hydroxy substituted stilbene derivatives in high purity with minimum side products.

Yet another object of the invention is to provide a process in which some of the to substrates and organic bases such as vanillin and piperidine are FEMA GRAS approved which makes the process safer and eco-friendly.

Yet another object of the invention is to provide a process wherein the ionic liquids used as solvents are recyclable.

Still another object of the invention is to provide a process which utilizes less or non-hazardous chemicals.

Still another object of the invention is to provide a process which requires cheaper chemical reagents.

Yet another object of the invention is to develop industrially viable and economical process towards formation of high valued 2- or 4-hydroxy substituted stilbene derivatives.

Yet another object of the invention is to develop a process wherein one of the benzaldehyde substrates used should have at least one hydroxy substitution at 2- or 4-position.

SUMMARY OF THE INVENTION

The present invention provides a process for the preparation of some novel commercially important multiconjugated 2- or 4-hydroxy substituted stilbene derivatives such as analogues of lithospermic acid, bis-styrylbenzenes, salvianolic acid, resveratrol, pterostilbene, and many others under microwave irradiation from the one pot multicomponent reaction of substituted arylaldehydes, malonic acid and halobenzenes with at least one hydroxy substituent at 2- or 4-position of arylaldehyde in the presence of a base, Pd catalyst, $PPh_3$ and solvent. The base is selected from a group consisting of collidine, triethylamine, pyridine, piperidine, sodium acetate, ammonium acetate, imidazole, methyl imidazoles, DBU and the like. Palladium catalyst is selected from a group consisting of palladium acetate, palladium nanoparticles, palladium chloride, tetrakis(triphenylphosphine)palladium(0) etc. Solvent for the process is selected from a group consisting of dimethylformamide, polyethylene glycol, dimethoxyethane, glycol, NMP, DMA, toluene, pyridine, ionic liquids and the like. The final products 2- or 4-hydroxy substituted stilbene derivatives are obtained in good to moderate yields varying from 25-66% within 1 min-16 hrs. It is worthwhile to mention that this microwave-assisted unique process is in fact an unexpected and novel result of three-four individual steps consisting of condensation of substituted arylaldehydes and malonic acid, decarboxylation and coupling of hydroxy styrene with halobenzenes occurring in one pot with at least one hydroxy substituent at 2- or 4-position of arylaldehyde without addition of any decarboxylating or protection-deprotection agents. It is also important to note that the developed one pot multicomponent process provides 2- or 4-hydroxy substituted stilbene derivatives in enhanced yields and reduced times in comparison to when the same reactions are conducted separately through the sequential isolation of reaction intermediates. Further that conducting the above reaction by conventional method instead of microwave provides the corresponding cinnamic acids as major products and low yield of stilbene derivatives, even when 2- or 4-hydroxy substituted arylaldehyde are taken as starting materials.

Accordingly, the present invention provides novel multi-conjugated hydroxy stilbene derivatives with the general formula 1:

Formula 1 wherein, at least one substituent being OH amongst $R_1$, $R_2$, $R_3$, $R_5$, $R_6$, $R_7$, $R_8$, $R_{10}$, and rest of substituents amongst $R_1$ to $R_{10}$, being H, OH, $OCH_3$, $CH_3COO$, halogen group, nitro group, $CH=CH-COOH$, $C_6H_3$-(4-OH,3-OMe), $C_6H_4-CH=CH-CO-C_6H_4$-(4-OMe), $CH_2-CH_2-CH_3$ or combinations thereof.

In an embodiment of the present invention, the representative compounds of the general formula 1 comprising;
 i. 4-((E)-prop-2-enoic acid)-3',4'-dihydroxystilbene,
 ii. 4-((E)-prop-2-enoic acid)-4'-hydroxy-3',5'-dimethoxystilbene,
 iii. 2'-(propyl)-4-hydroxy-3,4',5'-trimethoxystilbene,
 iv. 4-hydroxy-3,4',5-trimethoxy stilbene,
 v. 4-hydroxy-3-methoxy, 3'4'-dioxymethylenestilbene,
 vi. 2-(4-hydroxy-3-methoxystyryl)thiophene,
 vii. (E,E)-1,4-Bis(4-hydroxy, 3-methoxy)styrylbenzene,
 viii. ((E,E)-1,4-Bis(4-hydroxy-3-methoxy)styrylbenzene,
 ix. ((E,E)-1,4-Bis(4-hydroxy-3,5-dimethoxy)styrylbenzene,
 x. ((E,E)-4,4'-Bis(4-hydroxy-3,5-dimethoxy)styrylbiphenyl,
 xi. ((E,E,E)-1,3,5-Tris(4-hydroxy-3,5-dimethoxy)styrylbenzene,
 xii. (E,E)-1,4-Dimethoxy-2,5-bis(4-hydroxy-3-methoxy)styryl-benzene,
 xiii. (E,E)-9,10-Bis(4-hydroxy-3,5-dimethoxy)styrylanthracene,
 xiv. (E,E)-2-Fluoro-1,4-bis(4-hydroxy-3,5-dimethoxy)styryl-benzene,
 xv. 4-hydroxy-3-methoxy-4'-(3-(1-(4-methoxyphenyl))-2-propen-1-one) stilbene.

In another embodiment of the present invention, the said process comprising the steps of:
 a) reacting substituted arylaldehyde with at least one hydroxy substituent at 2- or 4-position, malonic acid and halobenzene in the presence of a base, palladium catalyst, triphenylphosphine and a solvent by refluxing under conventional or microwave irradiation for a period ranging between 30 min-15 hr.
 b) transferring the reaction mixture of step (a) and washing the residue with an organic solvent,
 c) washing the organic solution of step (b) with a mineral acid, brine and water,
 d) drying the organic layer of step (c) over a dehydrating agent, filtering and evaporating to dryness to completely remove the solvent to obtain a residue,
 e) purifying the residue of step (d) on Si-gel (60-120 mesh size) with a mixture of ethylacetate and hexane (9:1 to 6:4) to obtain the required substituted 2-aryl aldehydes of general formula 1.

In yet another embodiment of the present invention, the base used is selected from the group consisting of collidine, triethylamine, pyridine, piperidine, DBU, sodium acetate, ammonium acetate, imidazole, methyl imidazoles, ammonium formate and a combination there of.

In yet another embodiment of the present invention, the palladium catalyst used is selected from the group consisting of palladium acetate, palladium nanoparticles, to palladium chloride, tetrakis(triphenylphosphine)palladium(0) and a combination there of.

In still another embodiment of the present invention, the solvent used is selected from the group consisting of dimethylformamide, polyethylene glycol, dimethoxethane, NMP, DMA, toluene, pyridine, ionic liquids and a combination there of.

In still another embodiment of the present invention, the mole ratio between substituted arylaldehyde and malonic acid is ranging between 1:1 to 1:4 moles.

In still yet another embodiment of the present invention, the mole ratio between the substituted arylaldehyde and the base is ranging between 1:1 to 1:6 moles, preferably, 1:3 moles.

In still yet another embodiment of the present invention, the mole ratio between the substituted arylaldehyde and halobenzene is ranging between 1:1 to 1:2 moles.

In further yet another embodiment of the present invention, the mole ratio between halobenzene and palladium catalyst is ranging between 1:0.01 to 1:0.04 moles.

In further another embodiment of the present invention, the mole ratio between halobenzene and triphenylphosphine is ranging between 1:0.01 to 1:0.05 moles.

In further another embodiment of the present invention, the claimed process is found workable in both monomode at 250 W and 160° C. temperature and multimode microwave at 700-1500 W and 160-180° C. temperatures.

In yet another embodiment of the present invention, the various substituted stilbene derivatives obtained by the developed process can also be hydrogenated in same pot to provide the biologically important bibenzyl derivatives.

In yet another embodiment of the present invention, the hydroxylated or methoxylated styrenes obtained in situ via decarboxylation of respective cinnamic acid derivatives also undergo multicomponent reaction of hydroxy substituted benzaldehydes in the same pot in the presence of an ionic liquid.

In further another embodiment of the present invention, the process for the preparation of 2- or 4-hydroxy substituted stilbene derivatives is carried out in a one pot multicomponent manner wherein condensation, decarboxylation and heck coupling occur simultaneously without either the need for decarboxylating/protection-deprotection agents or individual isolation of highly reactive intermediates in one step.

BRIEF DESCRIPTION OF THE DRAWINGS

Aspects of the present invention are illustrated by way of example and not limited in the accompanying figures, in which.

DETAILED DESCRIPTION OF THE INVENTION

The one pot multicomponent approach was found to be particularly useful for the expedite synthesis of various multiconjugated stilbene derivatives which are conventionally synthesized through lengthy and inefficient multistep protocols. It is worthwhile to mention that the developed one pot multicomponent process provides 2- or 4-hydroxy substituted stilbene derivatives in enhanced yields and reduced time in comparison to when the same reactions are conducted separately through the sequential isolation of reaction intermediates. In addition, the reaction was also performed under refluxing on heating mantle instead of microwave conditions (Example V) and stilbene was obtained but in low yield along with the corresponding cinnamic acids. This clearly shows that microwave enhances the yield of product besides reducing the reaction time. As a corollary to our above success with direct one pot synthesis of stilbenes from benzaldehydes, we reasoned that the various bioactive stilbenes could also be accessed from the readily available cinnamic acids through a one pot decarboxylation-heck coupling strategy. Thus, the one pot decarboxylation of ferulic acid and its heck coupling with iodoanisole was explored in the presence of a base, palladium catalyst, triphenylphosphine and various solvents like DMSO, DMF, ionic liquids etc. We were indeed gratified when the above one pot approach was also able to provide the expected stilbene while the ionic liquids were found to be the optimum solvents for above transformation. Interestingly, the above method was also found to be applicable for synthesis of methoxylated stilbene derivatives through a one pot decarboxylation of methoxylated cinnamic acids and their subsequent heck coupling with iodoanisole. It is pertinent to mention that the developed methodology was also found to be useful for the synthesis of 2'-(2-propanoic acid)-4-hydroxy-3,3',4'-trimethoxystilbene and related compounds through the treatment of corresponding 2-(2-bromo-4,5-dimethoxyphenyl)propanoic acid with vanillin and malonic acid in the presence of a base, palladium catalyst and triphenylphosphine under microwave irradiation. Similarly, the synthetically important 4-carboxaldehyde-4'-hydroxystilbene could also be easily accessed by treatment of 4-hydroxystyrene with iodobenzaldehyde. It would be worthwhile to mention here that our above explorations regarding one pot decarboxylation-heck reaction or palladium catalyzed coupling of two aromatic acids through their simultaneous decarboxylation led us to a curious observation wherein the treatment of 4-hydroxy phenyl propionic acid with a base in the presence of ionic liquid [bmim]Br at 180-240° C. under microwave led to the unexpected formation of corresponding methyl ester i.e. methyl 4-hydroxy phenylpropionate. We were quite intrigued with above finding and reasoned that the methyl group for above esterification might result from a microwave induced degradation of [bmim] [Br]. Interestingly, our above premise was confirmed when the $H^1$ nmr analysis of ionic liquid recovered from above reaction revealed it to be butylimidazolium bromide thus indicating a unique demethylation of the [bmim] [Br] ionic liquid in the presence of microwave. It may be mentioned here that the above unexpected demethylation of ionic liquid could be a useful synthetic tool for the synthesis of various aromatic esters as well as methylation of phenols/thiophenols etc. In addition, the above finding points to a hitherto unrecognized fact regarding temperature (>180° C.) induced degradation of ionic liquids which needs to be properly look into for the proper utilization of ionic liquid induced chemical transformations including heck coupling etc.

It is pertinent to mention that in the course of above investigations into one pot multicomponent synthesis of various stilbene derivatives, our attention was also drawn to the possibility of a one pot condensation-decarboxylation-hydrogenation strategy leading to a convenient synthesis of bibenzyl derivatives which also possess important biologically activities (*J. Nat. Prod.* 2007, 70, 24-28; *J. Org. Chem.* 2007, 72, 2251-2254). Consequently, vanillin and phenyl acetic acid were reacted in the presence of an aqueous base and palladium catalyst and the formation of corresponding bibenzyl derivative was confirmed by NMR investigations.

In conclusion, our invention discloses a simple and economical process for preparing some novel multiconjugated commercially important 2- or 4-hydroxy substituted stilbene derivatives starting from relatively cheaper and economical material substituted arylaldehydes, malonic acid and substituted halo benzenes with at least one hydroxy substituent at 2- or 4-position of the arylaldehyde in the presence of a base, palladium catalyst, triphenylphosphine and a solvent under microwave or conventional conditions which dispenses with the hitherto indispensable requirement for multistep synthesis involving tedious and synthetically inefficient isolation of reaction intermediates obtained from sequential condensation-decarboylation and Heck reactions, harsh protection-deprotection steps besides eliminating the use or a decarboxylating agent.

The methodology involves a one pot multicomponent reaction between substituted arylaldehydes, an active methylene compound and various halobenzene derivatives with at least one hydroxy substituent at 2- or 4-position of an arylaldehyde under microwave irradiation using base, $Pd(OAc)_2$, $PPh_3$ and solvent. The reaction proceeds smoothly through a unique simultaneous condensation, decarboxylation, Heck coupling and dispenses with the hitherto indispensable requirement for linear multistep synthesis involving tedious and synthetically inefficient isolation of reaction intermediates obtained from sequential condensation, decarboxylation, Heck reactions, harsh protection-deprotection steps besides providing the desired hydroxy stilbene derivatives in improved yields and shorter reaction times as compared to the conventional protocols.

The invention is further illustrated with the help of the following examples and should not be construed to limit the scope of the present invention.

Example I

Synthesis of 4-hydroxy-3,4'-dimethoxy stilbene

Under Monomode Microwave (from formula I where $R_3$=OH, $R_4$=$R_3$=OMe, $R_1$, $R_2$, $R_3$, $R_5$, $R_6$, $R_9$, $R_{10}$=H):

A mixture of 4-hydroxy-3-methoxybenzaldehyde (3.42 mmol), malonic acid (13.68 mmol), para-iodo anisole (1.9 mmol), palladium acetate (0.076 mmol), triphenylphosphine (0.089 mmol), piperidine (15.58 mmol) and DMF (20 ml) were taken in a 100 ml round bottom flask fitted with a condenser. The flask was shaken well and placed inside the monomode microwave oven and irradiated (250 W, 160° C.) for 30 minutes in parts. After completion, the reaction mixture was poured in ice cooled water and extracted with ethyl acetate. The organic layer was washed with dil. HCl, brine and water and dried over sodium sulphate. The solvent was evaporated under reduced pressure to obtain liquid which was purified on silica gel by column chromatography using a mixture of hexane and ethyl acetate (9:1 to 6:4), provided a white solid; 40% yield (m.p. 163-166° C.); $^1$H NMR (CDCl$_3$) 7.36 (2H, d), 6.94 (2H, m), 6.83 (5H, m), 5.59 (1H, s), 3.86 (3H, s), 3.75 (3H, s); $^{13}$C NMR (CDCl$_3$) 159.0, 146.7, 145.2, 130.3, 127.4, 126.6, 126.1, 120.1, 114.5, 114.1, 108.0, 55.9 and 55.3. The above reaction was also found to be feasible under multimode microwave.

Example II

Synthesis of 4-hydroxy-3,4'-dimethoxy stilbene

Using Recyclable Palladium Nanoparticle and in Absence of Toxic Triphenyl Phosphine (from formula I where $R_3$=OH, $R_4$=$R_3$=OMe, $R_1$, $R_2$, $R_3$, $R_5$, $R_6$, $R_9$, $R_{10}$=H):

Palladium acetate (0.1 mmol) was added to a rapidly stirring solution of PEG (0.75 mmol) taken in a 100 ml round bottom flask and the contents were subsequently heated at 80° C. for 2 hours. The heating was stopped after 2 hours with the formation of brown palladium nanoparticles. The mixture was allowed to cool to room temperature. A mixture of 4-hydroxy-3-methoxybenzaldehyde (3.42 mmol), malonic acid (13.68 mmol), para-iodo anisole (1.9 mmol), palladium nanoparticles (0.078 mmol), piperidine (15.58 mmol) and DMF (20 ml) were taken in a 100 ml round bottom flask fitted with a condenser. The flask was shaken well and placed inside the monomode microwave oven and irradiated (250 W, 160° C.) for 30 minutes in parts. After completion, the reaction mixture was extracted with diethyl ether and palladium nanoparticle was recovered as insoluble fine particles to be used in the next cycle. The organic layer was washed with dil. HCl, brine and water and dried over sodium sulphate. The solvent was evaporated under reduced pressure to obtain liquid which was purified on silica gel by column chromatography using a mixture of hexane and ethyl acetate (9:1 to 6:4), provided a white solid; 35% yield (m.p. 163-166° C.); $^1$H NMR (CDCl$_3$) 7.36 (2H, d), 6.94 (2H, m), 6.83 (5H, m), 5.59 (1H, s), 3.86 (3H, s), 3.75 (3H, s); $^{13}$C NMR (CDCl$_3$) 159.0, 146.7, 145.2, 130.3, 127.4, 126.6, 126.1, 120.1, 114.5, 114.1, 108.0, 55.9 and 55.3.

Example III

Synthesis of 4-hydroxy-3,4'-dimethoxy stilbene

Under Conventional Heating (from formula I where $R_3$=OH, $R_4$=$R_8$=OMe, $R_1$, $R_2$, $R_3$, $R_5$, $R_6$, $R_9$, $R_{10}$=H):

A mixture of 4-hydroxy-3-methoxybenzaldehyde (3.42 mmol), malonic acid (13.68 mmol), para-iodoanisole (1.9 mmol), palladium acetate (0.076 mmol), triphenylphosphine (0.089 mmol), piperidine (15.58 mmol) and DMF (25 ml) were taken in a 100 ml round bottom flask and refluxed the mixture. After completion, the reaction was worked up as in example I and provided a white solid; 35% yield (m.p. 163-166° C.); $^1$H NMR (CDCl$_3$) 7.36 (2H, d), 6.94 (2H, m), 6.83 (5H, m), 5.59 (1H, s), 3.86 (3H, s), 3.75 (3H, s); $^{13}$C NMR (CDCl$_3$) 159.0, 146.7, 145.2, 130.3, 127.4, 126.6, 126.1, 120.1, 114.5, 114.1, 108.0, 55.9 and 55.3.

Example IV

Synthesis of 4-hydroxy-3,4'-dimethoxy stilbene

Via Sequential Isolation/Reaction of Hydroxy Styrene (From formula I where $R_3$=OH, $R_4$=$R_8$=OMe, $R_1$, $R_2$, $R_3$, $R_5$, $R_6$, $R_9$, $R_{10}$=H):

A mixture of 4-hydroxy-3-methoxybenzaldehyde (3.42 mmol), malonic acid (13.68 mmol), piperidine (15.58 mmol) in DMF (20 ml) were taken in a 100 ml round bottom flask fitted with a condenser. The flask was shaken well and placed inside the monomode microwave oven and irradiated (250 W, 160° C.) for 15 minutes in parts. After completion, the reaction mixture was poured in ice cooled water and extracted with ethyl acetate. The organic layer was washed with dil. HCl, brine and water and dried over sodium sulphate. The solvent was evaporated under reduced pressure to obtain liquid which was purified on silica gel by column chromatography using a mixture of hexane and ethyl acetate (9:1 to 6:4), provided 4-hydroxy-3-methoxystyrene, a sweet and pleasant smelling liquid, in 51% yield; $^1$H NMR (CDCl$_3$) 7.36 (21-1, d), 6.94 (2H, m), 6.83 (5H, m), 5.59 (1H, s), 3.86 (3H, s), 3.75 (3H, s); $^{13}$C NMR (CDCl$_3$) 159.0, 146.7, 145.2, 130.3, 127.4, 126.6, 126.1, 120.1, 114.5, 114.1, 108.0, 55.9 and 55.3.

Alternatively, the above 4-hydroxy, 3-methoxystyrene was also obtained using a mild base like ammonium formate in the presence of an ionic liquid.

The obtained 4-hydroxy, 3-methoxystyrene was taken in a 100 ml round bottom flask fitted with a condenser and mixed with para-iodo anisole (1.9 mmol), piperidine (4.5 mmol), palladium acetate (0.076 mmol), triphenylphosphine (0.089 mmol) and DMF (20 ml). The flask was shaken well and placed inside the monomode microwave oven and irradiated (250 W, 160° C.) for 30 minutes in parts. After completion, the reaction mixture was poured in ice cooled water and extracted with ethyl acetate. The organic layer was washed with dil. HCl, brine and water and dried over sodium sulphate. The solvent was evaporated under reduced pressure to obtain liquid which was purified on silica gel by column chromatography using a mixture of hexane and ethyl acetate (9:1 to 6:4)

provided a white solid; 50% yield (20% overall yield starting from vanillin) (m.p. 163-166° C.); $^1$H NMR (CDCl$_3$) δ 7.37 (2H, d), 6.95 (2H, d,), 6.84 (5H, m), 3.88 (3H, s), 3.76 (3H, s); $^{13}$C NMR (CDCl$_3$) δ 159.0, 146.7, 145.3, 130.4, 127.4, 126.6, 126.1, 120.1, 114.5, 114.1, 108.0, 55.9 and 55.3.

Example V

Synthesis of 4-((E)-prop-2-enoic acid)-3',4'-dihydroxystilbene

Figure 1:
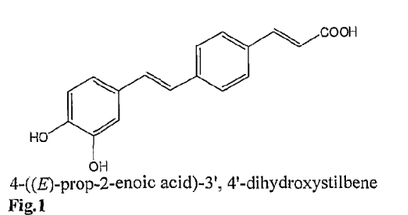
FIG. 1 is a diagram illustrating a chemical structure of 4-((E)-prop-2-enoic acid)-3', 4'-dihydroxystilbene.

Lithospermic Acid F Analogue—FIG. 1

(from formula I where $R_2=R_3=$OH and $R_8=$CH=CH—COOH, $R_1$, $R_4$, $R_5$, $R_6$, $R_7$, $R_9$, $R_{10}=$H):

A mixture of 3,4-dihydroxybenzaldehyde (4.05 mmol), malonic acid (27 mmol), 4-bromobenzaldehyde (2.7 mmol), palladium acetate (0.08 mmol), triphenylphosphine (0.14 mmol), piperidine (35.1 mmol) and DMF (20 ml) were taken in a 100 ml round bottom flask fitted with a condenser. The flask was shaken well and placed inside the monomode microwave oven and irradiated (250 W, 160° C.) for 30 minutes in parts. After completion, the reaction was worked up as in example I and provided a yellow solid; 45% yield (m.p. 260-263° C.); $^1$H NMR (300 MHz, DMSO) δ 7.58-7.47 (5H, m), 7.08 (1H, d,), 6.94 (1H, s), 6.89-6.80 (2H, m) 6.77 (1H, d), 6.45 (1H, d): $^{13}$C NMR (75.4 MHz, DMSO), δ$_C$ 168.2, 146.4, 145.9, 144.1, 140.0, 133.1, 130.7, 129.3, 129.1, 126.9, 124.7, 119.4, 118.7, 116.2 and 113.9.

Example VI

Synthesis of 4-((E)-prop-2-enoic acid)-4'-hydroxy-3',5'-dimethoxystilbene

Figure 2:
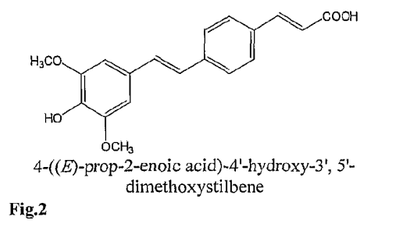
FIG. 2 is a diagram illustrating a chemical structure of 4-((E)-prop-2-enoic acid)-4'-hydroxy-3', 5'-dimethoxystilbene.

Lithospermic Acid F Analogue—FIG. 2

(From formula I where $R_3=$OH, $R_2=R_4=$OCH$_3$ and $R_8=$CH=CH—COOH, $R_1$, $R_5$, $R_6$, $R_7$, $R_9$, $R_{10}=$H):

A Mixture of 4-hydroxy-3,5-dimethoxybenzaldehyde (4 mmol), malonic acid (27 mmol), 4-bromobenzaldehyde (2.7 mmol), palladium acetate (0.08 mmol), triphenylphosphine (0.14 mmol), piperidine (35.1 mmol) and DMF (20 ml) were taken in a 100 ml round bottom flask fitted with a condenser. The flask was shaken well and placed inside the monomode microwave oven and irradiated (250 W, 160° C.) for 30 minutes in parts. After completion the reaction was worked up as in example I and provided a yellow solid; 60% yield (m.p. 202-207° C.); $^1$H NMR (300 MHz, DMSO) 7.68-7.55 (5H, m), 7.27 (1H, d), 7.17 (1H, d), 6.92 (2H, s), 6.54 (1H d), 3.81 (6H, s): $^{13}$C NMR (75.4 MHz, DMSO) δ$_C$ 168.2, 148.5, 144.0, 140.0, 136.5, 132.2, 130.9, 129.2, 127.8, 126.9, 125.4, 118.8, 104.8 and 56.4.

Example VII

Synthesis of 4-chloro-4'-hydroxyl-3'-methoxystilbene (from formula I where $R_3=$OH, $R_4=$OCH$_3$ and $R_8=C_1$, $R_1$, $R_2$, $R_5$, $R_6$, $R_7$, $R_9$, $R_{10}=$H):

A mixture of 4-hydroxy-3-methoxybenzaldehyde (3.42 mmol), malonic acid (13.68 mmol), 4-chloro-iodobenzene (1.9 mmol), palladium acetate (0.076 mol), triphenylphosphine (0.089 mmol), piperidine (15.58 mmol) and DMF (20 ml) were taken in a 100 ml round bottom flask fitted with a condenser. The flask was shaken well and placed inside the monomode microwave oven and irradiated (250 W, 160° C.) for 30 minutes in parts. After completion, the reaction was worked up as in example I and provided a white solid; 48% yield (m.p. 121-124° C.); $^1$H NMR (CDCl$_3$) δ 7.35 (21-1, d), 7.25 (2H, d,), 6.96 (3H, m), 6.87 (2H, m), 5.72 (1H, s), 3.87 (3H, s); $^{13}$C NMR (75.4 MHz, CDCl$_3$) δ$_C$ 146.8, 145.8, 136.1, 132.7, 129.6, 129.2, 128.8, 127.4, 125.1, 120.6, 114.6, 108.3 and 55.9.

Example VIII

Synthesis of 2'-(propyl)-4-hydroxy-3,4',5'-trimethoxystilbene

Figure 3:
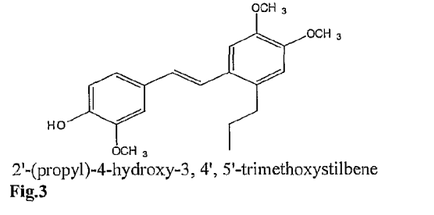
FIG. 3 is a diagram illustrating a chemical structure of 2'-(propyl)-4-hydroxy-3,4', 5'-*trimethoxystilbene*.

FIG. 3

(From formula I where $R_3=$OH, $R_6=$CH$_2$—CH$_2$—CH$_3$, $R_4=R_8=R_9=$OCH$_3$, and $R_1$, $R_2$, $R_5$, $R_7$, $R_{10}=$H):

A mixture of 4-hydroxy-3-methoxybenzaldehyde (3.47 mmol), malonic acid (13.8 mmol), 2-bromo-4,5-dimethoxypropylbenzene (1.93 mmol), palladium acetate (0.09 mmol), triphenylphosphine (0.14 mmol), piperidine (15.8 mmol) and DMF (20 ml) were taken in a 100 ml round bottom flask fitted with a condenser. The flask was shaken well and placed inside the monomode microwave oven and irradiated (250 W, 160° C.) for 30 minutes in parts. After completion the reaction was worked up as in example I and provided a white crystalline solid; 25% yield (m.p. 74-78° C.); $^1$H NMR (300 MHz, CDCl$_3$) δ 7.11-6.93 (4H, m), 6.86 (1H, d), 6.78 (1H, d), 6.61 (1H, s), 5.62 (1H, s), 3.88 (3H, s), 3.86 (3H, s), 3.78 (3H, s), 2.61 (2H, t), 1.55 (2H, m), 0.91 (31-1, t): δ$_C$ (75.4 MHz, CDCl$_3$) δ$_C$ 148.4, 147.3, 146.7, 145.3, 133.2, 130.7, 128.3, 127.9, 124.2, 119.8, 114.6, 112.8, 108.6, 108.5, 56.0, 35.1, 24.7 and 14.0. The above obtained hydroxystilbene derivative was alkylated or acetylated/benzoylated in the same pot with addition of alkyl halide or acetyl chloride or benzoyl chloride etc.

Example IX

Synthesis of 4-hydroxy-3,4',5-trimethoxy stilbene

Figure 4:
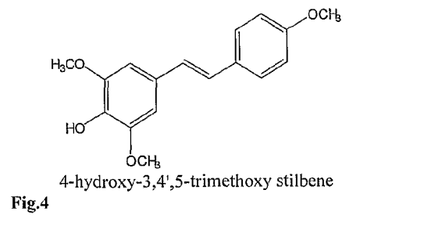
FIG. 4 is a diagram illustrating a chemical structure of 4-hydroxy-3,4',5-trimethoxy stilbene.

FIG. 4

(From formula I where $R_3=$OH, $R_2=R_4=R_5=$OCH$_3$ and $R_1$, $R_5$, $R_6$, $R_7$, $R_9$, $R_{10}=$H):

A mixture of 4-hydroxy-3,5-dimethoxybenzaldehyde (15.38 mmol), malonic acid (61.52 mmol), 4-iodoanisole (8.54 mmol), palladium acetate (0.34 mmol), triphenyl phosphine (0.58 mmol), piperidine (70.07 mmol) and DMF (42 ml) were taken in a 150 ml round bottom flask fitted with a condenser. The flask was shaken well and refluxed for 11 hours. After completion the reaction was worked up as in example I to provide a white solid; 39% yield (m.p 96-98° C.); H$^1$ NMR (CDCl$_3$, 300 MHz) δ 7.46 (2H, d), 6.98-6.90 (4H, m), 6.75 (2H, s), 5.60 (1H, s), 3.96 (6H, s), 3.85 (3H, s); $^{13}$C NMR (CDCl$_3$, 75.4 MHz) 159.2, 147.3, 134.6, 130.3, 129.4, 127.5, 126.9, 126.5, 114.2, 103.2, 56.4 and 55.4.

Example X

Synthesis of 4-hydroxy-3-methoxy, 3',4'-dioxymethylenestilbene

Figure 5:
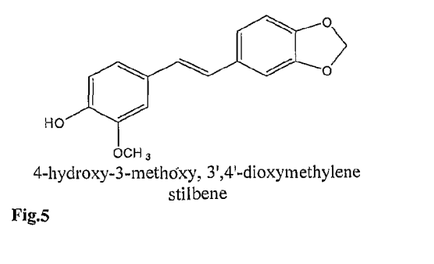
FIG. 5 is a diagram illustrating a chemical structure of 4-hydroxy-3-methoxy,3'4'-dioxymethylenestilbene.

FIG. 5

(From formula I where $R_3=$OH, $R_4=$OCH$_3$, $R_8=R_9=$OCH$_2$O and $R_1$, $R_2$, $R_5$, $R_6$, $R_7$, $R_{10}=$H):

A mixture of 4-hydroxy-3-methoxybenzaldehyde (17.90 mmol), malonic acid (71.63 mmol), 1-bromo-3,4-(dioxymethylene)benzene (9.95 mmol), palladium acetate (0.29 mmol), triphenyl phosphine (0.51 mmol), piperidine (81.59 mmol) and DMF (42 ml) were taken in a 150 ml round bottom flask fitted with a condenser. The flask was shaken well and refluxed for 10 hours. After completion the reaction was worked up as in example I to provide a white solid; 35% yield (m.p 151-156° C.); $H^1$ NMR (CDCl$_3$, 300 MHz), δ 7.63 (1H, s), 7.17 (1H, s), 7.10 (1H, s), 6.97-6.91 (4H, m), 6.79 (214, d), 5.96 (2H, s), 3.85 (3H, s); $^{13}$C NMR (CDCl$_3$, 75.4 MHz) 148.3, 147.7, 147.0, 146.5, 132.5, 129.7, 127.1, 125.6, 120.9, 120.0, 115.0, 109.1, 108.2, 105.0, 100.8 and 55.3.

Example XI

Synthesis of 2-(4-hydroxy-3-methoxystyryl)thiophene

Figure 6:
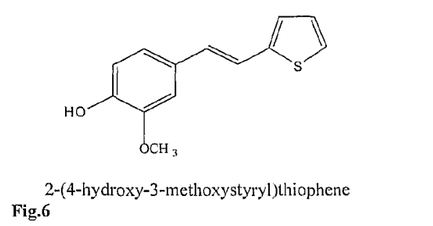
FIG. 6 is a diagram illustrating a chemical structure of 2-(4-hydroxy-3-methoxystyryl) thiophene.

FIG. 6

A mixture of 4-hydroxy-3-methoxybenzaldehyde (8.56 mmol), malonic acid (34.27 mmol), 2-iodothiophene (4.76 mmol), palladium acetate (0.19 mmol), triphenyl phosphine (0.321=01), piperidine (39.04 mmol) and DMF (30 ml) were taken in a 100 ml round bottom flask fitted with a condenser. The flask was shaken well and refluxed for 9 hours. After completion the reaction was worked up as in example I to provide a viscous solid; 28% yield; $H^1$ NMR (CDCl$_3$, 300 MHz), δ 7.19 (1H, s), 7.15 (1H, d), 7.06-7.01 (4H, m), 6.65-6.86 (2H, m), 5.75 (1H, s), 3.95 (3H, s); $^{13}$C NMR (CDCl$_3$, 75.4 MHz) 146.8, 145.7, 143.2, 129.7, 128.5, 127.7, 125.5, 123.9, 120.3, 119.8, 114.7, 108.2 and 56.0.

Example XII

Synthesis of 1-(4-Methoxyphenyl)-2-(2-naphthyl)ethene

Figure 7:
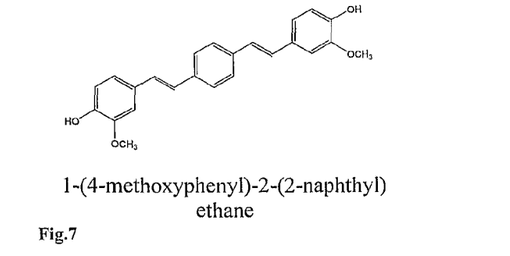
FIG. 7 is a diagram illustrating a chemical structure of 1-(4-methoxyphenyl)-2-(2-naphthyl)ethane.

Via One Pot Dehydration-Heck Coupling in the Presence of Ionic Liquid—FIG. 7

(from formula I where $R_2$=$R_3$=(CH=CH—CH=CH) and $R_8$=OMe, $R_1$, $R_4$, $R_5$, $R_6$, $R_7$, $R_9$, $R_{10}$=H):

A mixture of 1-(naphthyl)-1-ethanol (3 mmol), p-iodo anisole (2 mmol), palladium acetate (0.08 mmol), triphenylphosphine (0.14 mmol), piperidine (2 mmol) and 1-hexyl-3-methyl imidazolium bromide (2 ml), DMF (8 ml) were taken in a 100 ml round bottom flask fitted with a condenser. The flask was shaken well and placed inside the monomode microwave oven and irradiated (250 W, 160° C.) for 30 minutes in parts. After completion, the reaction was worked up as in example I and provided a white crystalline solid; 30% yield. m.p (162-164° C.) $^1$H NMR (CDCl$_3$) δ 7.87 (1H, s), 7.79-7.77 (4H, m), 7.52 (2H, d), 7.41-7.34 (2H, m), 7.30 (1H, d), 7.20 (1H, d), 6.90 (2H, d), 3.69 (3H, s); $^{13}$C NMR (CDCl$_3$) δ 159.5, 135.5, 133.8, 132.8, 130.1, 129.1, 128.6, 128.3, 128.2, 128.0, 126.9, 126.5, 126.2, 124.0, 114.7 and 55.6.

Example XIII

Synthesis of (E,E)-1,4-Bis(4-hydroxy-3-methoxy)styrylbenzene

Figure 8:
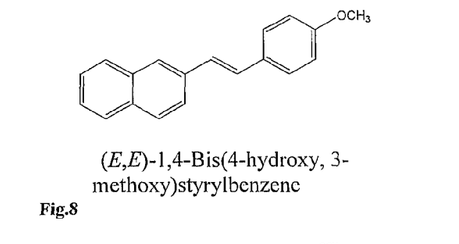
FIG. 8 is a diagram illustrating a chemical structure of (E,E)-1,4-Bis(4-hydroxy,3-methoxy)styrylbenzene.

FIG. 8

(From formula I where $R_3$=($C_6H_3$-(4-OH,3-OMe)CH=CH), $R_8$=OH, $R_9$=OCH$_3$ and, $R_1$, $R_2$, $R_4$, $R_5$, $R_6$, $R_7$, $R_{10}$=H):

A mixture of 4-hydroxy-3-methoxybenzaldehyde (10.91 mmol), malonic acid (43.63 mmol), diiodobenzene (3.03 mmol), palladium acetate (0.24 mmol), triphenyl phosphine (0.41 mmol), piperidine (46.66 mmol) and DMF (35 ml) were taken in a 100 ml round bottom flask fitted with a condenser. The flask was shaken well and refluxed for 10 hours. After completion the reaction was worked up as in example I to provide a grey solid; 52% yield (m.p 266-270° C.); $H^1$ NMR (DMSO, 300 MHz), δ 9.16 (2H, s), 7.52 (4H, s), 7.20 (2H, s), 7.18-7.02 (4H, m), 7.01 (2H, d), 6.79 (2H, d), 3.83 (6H, s); $^{13}$C NMR (DMSO, 75.4 MHz) 148.3, 147.1, 136.7, 129.2, 129.8, 127.4, 125.5, 120.6, 116.8, 110.2 and 55.3.

Example XIV

Synthesis of (E,E)-1,4-Bis(4-hydroxy-3,5-dimethoxy)styrylbenzene

Figure 9:
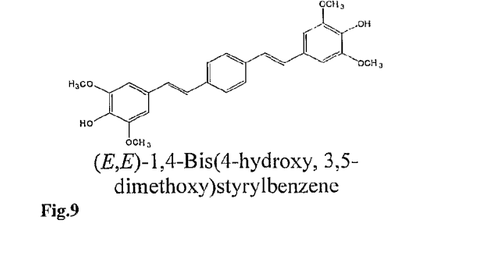
FIG. 9 is a diagram illustrating a chemical structure of ((E,E)-1,4-Bis(4-hydroxy-3,5-dimethoxy)styrylbenzene.

FIG. 9

(From formula I where $R_3$=($C_6H_2$-(4-OH, 3,4-OMe)CH=CH—), $R_8$=OH, R7=R9=OCH$_3$ and $R_1$, $R_2$, $R_4$, $R_5$, $R_6$, $R_{10}$=H):

A mixture of 4-hydroxy-3,5-dimethoxybenzaldehyde (10.90 mmol), malonic acid (43.63 mmol), 1,4-diiodobenzene (3.03 mmol), palladium acetate (0.24 mmol), triphenyl phosphine (0.41 mmol), piperidine (46.66 mmol) and DMF (35 ml) were taken in a 100 ml round bottom flask fitted with a condenser. The flask was shaken well and refluxed for 10 hours. After completion the reaction was worked up as in Example I to provide a greenish brown solid; 55% yield (m.p 245-250° C.); $H^1$ NMR (DMSO, 300 MHz) δ 8.45 (2H, s), 7.46 (4H, s), 7.05 (4H, s), 6.82 (4H, s), 3.74 (12H, s); $^{13}$C NMR (DMSO, 75.4 MHz) 148.6, 136.8, 136.3, 129.1, 128.1, 125.9, 124.6, 104.7 and 55.7.

Example XV

Synthesis of (E,E)-4,4'-Bis(4-hydroxy-3,5-dimethoxy)styrylbiphenyl

Figure 11:
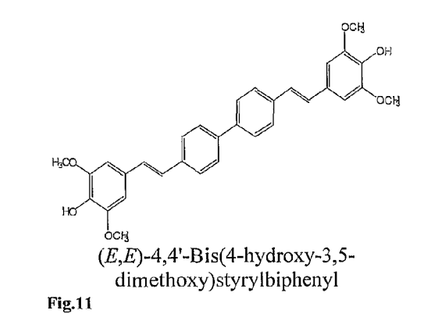
FIG. 11 is a diagram illustrating a chemical structure of (E,E)-4,4'-Bis(4-hydroxy-3,5-dimethoxy)styrylbiphenyl.

FIG. 11

(From formula I where $R_3$=($C_6H_2$-(4-OH,3,5-OMe)—CH=CH—$C_6H_4$), $R_8$=014, $R_7$=$R_9$=OCH$_3$ and, $R_1$, $R_2$, $R_4$, $R_5$, $R_6$, $R_{10}$=H):

A mixture of 4-hydroxy-3,5-dimethoxybenzaldehyde (8.86 mmol), malonic acid (35.46 mmol), 4,4'-diiodobiphenyl (2.46 mmol), palladium acetate (0.19 mmol), triphenyl phosphine (0.33 mmol), piperidine (37.93 mmol) and DMF (35 ml) were taken in a 100 ml round bottom flask fitted with a condenser. The flask was shaken well and refluxed for 10 hours. After completion the reaction was worked up as in example I to provide a yellowish brown solid; 52% yield (imp 277-280° C.); $H^1$ NMR (DMSO, 300 MHz), δ 8.58 (2H, s), 7.74 (4H, d), 7.65 (4H, d), 7.19 (4H, s), 6.93 (4H, s), 3.83 (12H, s); $^{13}$C NMR (DMSO, 75.4 MHz) 148.1, 138.0, 136.6, 135.8, 129.1, 127.5, 126.6, 125.1, 104.2 and 56.0.

Example XVI

Synthesis of (E,E,E)-1,3,5-Tris(4-hydroxy-3,5-dimethoxy)styrylbenzene

Figure 10:
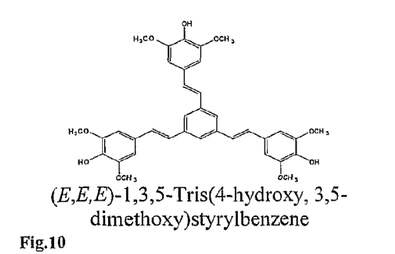
FIG. 10 is a diagram illustrating a chemical structure of (E,E,E)-1,3,5-Tris(4-hydroxy-3,5-dimethoxy)styrylbenzene.

FIG. 10

(From formula I where $R_2$=$R_4$=($C_6H_3$-(4-OH,3,5-OMe)CH=CH), $R_8$=OH, R7=R9=OCH$_3$ and $R_1$, $R_2$, $R_4$, $R_5$, $R_6$, $R_{10}$=H):

A mixture of 4-hydroxy-3,5-dimethoxybenzaldehyde (8.57 mmol), malonic acid (34.30 mmol), 1,3,5-tribromobenzene (1.58 mmol), Tetrakis(triphenylphosphine)palladium (0) (0.17 mmol), piperidine (36.05 mmol) and DMF (40 ml) were taken in a 100 ml round bottom flask fitted with a condenser. The flask was shaken well and refluxed for 10 hours. After completion the reaction was worked up as in example I to provide a yellow solid; 37% yield (m.p 223-225° C.); $H^1$ NMR (CDCl$_3$, 300 MHz), δ 7.53 (3H, s), 7.17 (3I-1, d), 7.04 (3H, d), 6.81 (6H, s), 5.62 (3H, s), 3.98 (18H, s); $^{13}$C NMR (CDCl$_3$, 75.4 MHz) 147.4, 138.3, 135.1, 129.4, 129.0, 126.7, 123.4, 103.6 and 56.5.

Example XVII

Synthesis of (E,E)-1,4-Dimethoxy-2,5-bis(4-hydroxy-3-methoxy)styryl-benzene

Figure 12:
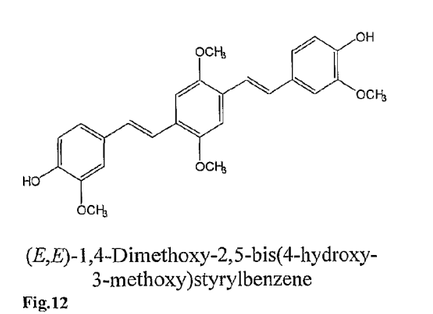
FIG. 12 is a diagram illustrating a chemical structure of (E,E)-1,4-Dimethoxy-2,5-bis(4-hydroxy-3-methoxy)styrylbenzene.

FIG. 12

(From formula I where $R_3$=(C$_6$H$_3$-(4-OH,3-OMe) CH=CH—), $R_1$=$R_4$=$R_9$=OCH3, $R_8$=OH and, $R_2$, $R_5$, $R_6$, $R_7$, $R_{10}$=H):

A mixture of 4-hydroxy-3-methoxybenzaldehyde (10.94 mmol), malonic acid (43.77 mmol), 1,4-dibromo-2,5-dimethoxybenzene (3.04 mmol), palladium acetate (0.24 mmol), triphenyl phosphine (0.41 mmol), piperidine (46.81 mmol) and DMF (35 ml) were taken in a 100 ml round bottom flask fitted with a condenser. The flask was shaken well and refluxed for 10 hours. After completion the reaction was worked up as in example I to provide a yellowish green solid; 39% yield (m.p 245-248° C.); $H^1$ NMR (DMSO, 300 MHz), δ 9.17 (2H, s), 7.24-7.21 (4H, m), 7.13 (2H, s), 7.00 (2H, s), 6.79 (2H, s), 3.89 (6H, s), 3.84 (6H, s); $^{13}$C NMR (DMSO, 75.4 MHz) 150.7, 147.7, 146.5, 129.1, 125.6, 119.6, 115.7, 110.0, 108.8, 56.0 and 55.5.

Example XVIII

Synthesis of (E,E)-9,10-Bis(4-hydroxy-3,5-dimethoxy)styrylanthracene

Figure 13:
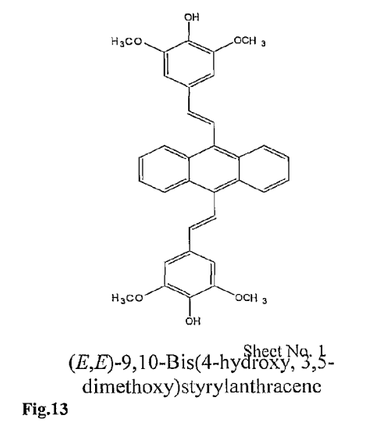
FIG. 13 is a diagram illustrating a chemical structure of (E,E)-9,10-Bis(4-hydroxy-3,5-dimethoxy)styrylanthracene.

FIG. 13

(From formula I where $R_3$=(C$_6$H$_2$-(4-OH,3,5-OMe) CH=CH—), $R_7$=$R_9$=OCH$_3$, $R_8$=OH and $R_1$=$R_2$=$R_4$=$R_5$=(CH=CH—CH=CH), $R_6$, $R_{10}$=H):

A mixture of 4-hydroxy-3,5-dimethoxybenzaldehyde (3.6 mmol), malonic acid (42.85 mmol), 9,10-dibromoanthracene (2.97 mmol), Tetrakis(triphenylphosphine) palladium(0) (0.16 mmol), piperidine (45.81 mmol) and DMF (35 ml) were taken in a 100 ml round bottom flask fitted with a condenser. The flask was shaken well and refluxed for 10 hours. After completion the reaction was worked up as in example I to provide a brown solid; 15% yield (m.p 212-216° C.); $H^1$ NMR (DMSO, 300 MHz), □ 8.62 (2H, s), 8.43 (4H, d), 8.03 (2H, d), 7.57-7.54 (4H, m), 7.11 (4H, s), 6.84 (2H, d), 3.87 (12H, s); $^{13}$C NMR (DMSO, 75.4 MHz) 148.2, 137.7, 136.0, 132.3, 129.0, 127.4, 126.3, 125.3, 121.8, 104.5 and 56.1.

Example XIX

Synthesis of (E,E)-2-Fluoro-1,4-bis(4-hydroxy-3,5-dimethoxy) styryl-benzene

Figure 14:
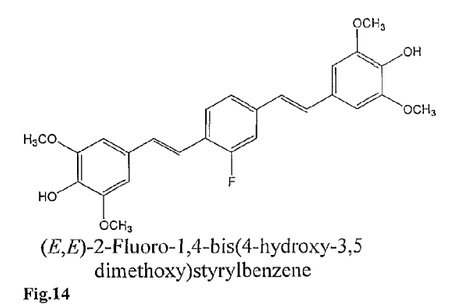
FIG. 14 is a diagram illustrating a chemical structure of (E,E)-2-Fluoro-1,4-bis(4-hydroxy-3,5-dimethoxy)styrylbenzene.

FIG. 14

(From formula I where $R_3$=(C$_6$H$_3$-(4-OH,3,5-OMe)— CH=CH—), $R_4$=F, $R_7$=$R_9$=OCH$_3$, $R_8$=OH, and, $R_1$, $R_2$, $R_5$, $R_6$, $R_{10}$=H):

A mixture of 4-hydroxy-3-methoxybenzaldehyde (14.17 mmol), malonic acid (56.59 mmol), 1,4-dibromo-2-fluorobenzene (3.93 mmol), palladium acetate (0.31 mmol), triphenyl phosphine (0.53 mmol), piperidine (60.65 mmol) and DMF (35 ml) were taken in a 100 ml round bottom flask fitted with a condenser. The flask was shaken well and refluxed for 10 hours. After completion the reaction was worked up as in example I to provide a yellow solid; 34% yield (m.p 225-227° C.); $H^1$ NMR (CD$_3$COCD$_3$, 300 MHz), □ 7.72 (1H, t), 7.49 (2H, s), 7.38-7.32 (2H, m), 7.27-7.21 (3H, m), 7.15 (1H, s), 6.96 (4H, s), 3.89 (12H, s); $^{13}$C NMR (CD$_3$COCD$_3$, 75.4 MHz) 148.8, 139.6, 139.5, 137.3, 132.0, 131.0, 129.0, 128.7, 127.7, 125.3, 124.7, 123.2, 118.4, 113.3, 113.0, 105.1 and 56.5.

Example XX

Synthesis of (E,E)-1,4-Bis(4-hydroxy)styrylbenzene (From formula I where $R_3$=(C$_6$H$_3$-(4-OH)CH=CH—), $R_8$=OH and $R_1$, $R_2$, $R_4$, $R_5$, $R_6$, $R_7$, $R_9$, $R_{10}$=H):

A mixture of 4-hydroxybenzaldehyde (10.91 mmol), malonic acid (43.64 mmol), diiodobenzene (3.03 mmol), palladium acetate (0.24 mmol), triphenyl phosphine (0.41 mmol), piperidine (46.66 mmol) and DMF (35 ml) were taken in a 100 ml round bottom flask fitted with a condenser. The flask was shaken well and refluxed for 10 hours. After completion the reaction was worked up as in example I to provide a grey solid; 48% yield; $H^1$ NMR (DMSO, 300 MHz), □ 9.68 (2H, s), 7.51-7.45 (8H, m), 7.13-7.04 (4H, m), 6.78 (4H, s); $^{13}$C NMR (DMSO, 75.4 MHz) 157.7, 136.7, 128.6, 128.5, 128.3, 126.8, 125.3, 116.0

Example XXI

Synthesis of 4-hydroxy-3-methoxy-4'-(3-(1-(4-methoxyphenyl))-2-propen-1-one) stilbene

Figure 15:
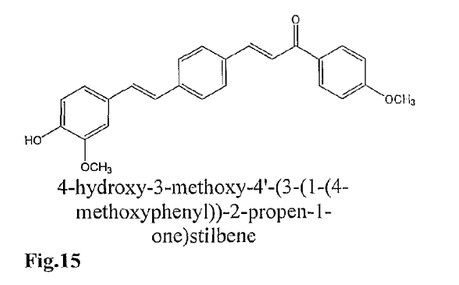
FIG. 15 is a diagram illustrating a chemical structure of 4-hydroxy-3-methoxy-4'-(3-(1-(4-methoxyphenyl))-2-propen-1-one)stilbene.

FIG. 15

(From formula I where $R_3$=OH, $R_4$=OCH$_3$ and $R_8$=C$_6$H$_4$—CH═CH—CO—C$_6$H$_4$-(4-OMe), $R_1$, $R_2$, $R_5$, $R_6$, $R_7$, $R_9$, $R_{10}$=H):

A mixture of 4-hydroxy-3-methoxybenzaldehyde (1.97 mmol), malonic acid (5.9 mmol), 4-bromo,4'-methoxychalcone (2.18 mmol), palladium acetate (0.057 mmol), triphenyl phosphine (0.099 mmol), piperidine (0.008 mmol) and DMF (20 ml) were taken in a 150 ml round bottom flask fitted with a condenser. The flask was shaken well and refluxed for 15 hours. After completion the reaction was worked up as in example I to provided a yellow solid 22% yield (m.p 175-179° C.); $^1$H NMR (CDCl$_3$, 300 MHz), 8.0 (2H, d), 7.76 (1H, d), 7.57 (2H, d), 7.50-7.44 (3H, m), 7.08 (1H, d), 6.99-6.84 (6H, m), 3.89 (3H, s), 3.83 (3H, s); $^{13}$C NMR (CDCl$_3$, 75.4 MHz) 188.7, 163.4, 146.8, 146.0, 143.6, 139.8, 133.9, 131.2, 130.8, 129.6, 128.9, 126.6, 125.6, 121.1, 120.8, 116.2, 114.6, 108.3, 55.9, and 55.5.

Example XXII

Synthesis of 4-Chloro 4'-hydroxy-3'-methoxy stilbene

Via Decarboxylation of Hydroxy Cinnamic Acid and Subsequent Heck Coupling in One Pot (from formula I where $R_3$=OH, $R_4$=OMe, Cl, $R_1$, $R_2$, $R_3$, $R_5$, $R_6$, $R_9$, $R_{10}$=H):

A mixture of 4-hydroxy-3-methoxycinnamic acid (1.88 mmol), (0.027 mol), 4-chloro-iodobenzene (1.25 mmol), palladium acetate (0.05 mmol), triphenyl phosphine (0.09 m mol), NaHCO$_3$ (1.88 mmol), Et$_3$N (2.5 mmol) and ionic liquid [hmim] [Br] (2 ml) were taken in a 100 ml round bottom flask fitted with a condenser. The flask was shaken well and placed inside the monomode microwave oven and irradiated (250 W, 160° C.) for 60 minutes in parts. After completion, the reaction was worked up as in example I to provide a white solid; 20% yield (m.p. 121-124° C.); $^1$H NMR (CDCl$_3$) □ 7.35 (2H, d), 7.25 (2H, d,), 6.96 (3H, m), 6.87 (2H, m), 5.72 (1H, s), 3.87 (3H, s); $^{13}$C NMR (CDCl$_3$) □ 146.8, 145.8, 136.1, 132.7, 129.6, 129.2, 128.8, 127.4, 125.1, 120.6, 114.6, 108.3 and 55.9.

The above methodology was also found to be applicable using DBU as a base instead of NaHCO$_3$.

The main advantages of the present invention are:

1. The main advantage of the present invention is to provide a method for the one pot multicomponent synthesis of hydroxy stilbene derivatives under microwave irradiation.
2. The present invention is to prepare some immensely important bioactive hydroxy stilbene derivatives including analogues of lithospermic acid (3,4-dihydroxy styrylcinnamate), bis-styrylbenzenes, salvionilic acid etc. by conducting a series of multicomponent reactions in the same pot.
3. A process for the preparation of 2- or 4-hydroxy substituted stilbene derivatives under microwave or conventional conditions.
4. A process for the preparation of 2- or 4-hydroxy substituted stilbene derivatives wherein condensation, decarboxylation and Heck coupling occurred in one step without addition of decarboxylating agent or the need for isolation of reaction intermediates.
5. A process to prepare 2- or 4-hydroxy substituted stilbene derivatives without the use of harsh protection-deprotection reagents.
6. A simple process for the preparation of 2- or 4-hydroxy substituted stilbene derivatives in high purity with minimum side products.
7. A process in which some of the substrates and organic bases such as vanillin and piperidine are FEMA GRAS approved which makes the process safer and eco-friendly.
8. A process wherein the ionic liquids used as solvents are recyclable.
9. Still another object of the invention is to provide a process which utilizes less or non-hazardous chemicals.
10. A process which requires cheaper chemical reagents.
11. It develops industrially viable and economical process towards formation of high valued 2- or 4-hydroxy substituted stilbene derivatives.

We claim:

1. A single step process for the preparation of some multi-conjugated hydroxy stilbene derivatives with the general formula 1:

Formula 1 wherein, at least one substituent being OH amongst R$_1$, R$_2$, R$_3$, R$_5$, R$_6$, R$_7$, R$_8$, R$_{10}$, and rest of substituents amongst R$_1$ to R$_{10}$, being H, OH, OCH$_3$, CH$_3$COO, halogen, nitro, CH=CH—COOH, C$_6$H$_3$ -(4-OH,3-OMe), C$_6$H$_4$—CH=CH—CO—C$_6$H$_4$-(4-OMe), CH$_2$—CH$_2$—CH$_3$, the said process comprising steps of:
(a) refluxing substituted arylaldehyde with at least one hydroxy substituent at 2- or 4-position, malonic acid and halobenzene in the presence of a base, palladium catalyst, triphenylphosphine and a solvent for a period ranging between 30 min-15 hr;
(b) transferring the reaction mixture of step (a) in ice cooled water and washing the residue with an organic solvent;
(c) washing the organic solution of step (b) with a mineral acid, brine and water;
(d) drying the organic layer of step (c) over a dehydrating agent, followed by filtering and evaporating to dryness to completely remove the solvent to obtain a residue;
(e) purifying the residue of step (d) on Si-gel (60-120 mesh size) with a mixture of ethylacetate and hexane (9:1 to 6:4) to obtain the required substituted hydroxy stilbene of general formula 1.

2. A process as claimed in claim 1, wherein the base used in step (a) is selected from the group consisting of collidine, triethylamine, pyridine, piperidine, DBU, sodium acetate, ammonium acetate, imidazole, methyl imidazoles, ammonium formate and a combination there-of.

3. A process as claimed in claim 1, wherein the palladium catalyst used in step (a) is selected from the group consisting of palladium acetate, palladium nanoparticles, palladium chloride, teterakis(triphenylphosphine) palladium-(0) and a combination thereof.

4. A process as claimed in claim 1, wherein solvent used in step (a) is selected from the group consisting of dimethylformamide, polyethylene glycol, dimethoxethane, NMP, DMA, toluene, pyridine, ionic liquids and a combination thereof.

5. A process as claimed in claim 1, wherein the mole ratio between substituted arylaldehyde and malonic acid is between 1:1 and 1:4 moles.

6. A process as claimed in claim 1, wherein the mole ratio between the substituted arylaldehyde and the base is between 1:1 and 1:6 moles.

7. A process as claimed in claim 1, wherein the mole ratio between the substituted arylaldehyde and halobenzene is between 1:1 and 1:2 moles.

8. A process as claimed in claim 1, wherein the mole ratio between halobenzene and palladium catalyst is between 1:0.01 and 1:0.04 moles.

9. A process as claimed in claim 1, wherein the mole ratio between halobenzene and triphenylphosphine is between 1:0.01 and 1:0.05 moles.

10. A process as claimed in claim 1, wherein the refluxing in step (a) is performed in both monomode at 250 W and 160° C. temperature and multimode microwave at 700-1500 W and 160-180° C. temperatures.

11. A process as claimed in claim 1, wherein the substituted stilbene compound is hydrogenated in same pot to provide the bibenzyl derivatives.

12. A process as claimed in claim 1, wherein hydroxylated or methoxylated styrenes obtained in situ via decarboxylation of cinnamic acid derivatives formed in step (a) also undergo multicomponent reaction with halobenzene in the same pot in the presence of an ionic liquid.

13. A process as claimed in claim 1, wherein the process for the preparation of 2- or 4-hydroxy substituted stilbene derivatives is carried out in a one pot multicomponent manner wherein condensation, decarboxylation and heck coupling occur simultaneously without either the need for decarboxylating/protection-deprotection agents or individual isolation of highly reactive styrene intermediates in one step.

* * * * *